(12) United States Patent
Buisson et al.

(10) Patent No.: US 9,308,178 B2
(45) Date of Patent: Apr. 12, 2016

(54) MICROCAPSULES CONTAINING AN OXIDIZABLE ACTIVE, AND A PROCESS FOR PREPARING THE SAME

(71) Applicant: IDCAPS, La Rochelle (FR)

(72) Inventors: Pierre Buisson, Lagord (FR); Carine Chaigneau, La Rochelle (FR); Jean-Eudes Vendeville, Perigny (FR)

(73) Assignee: IDCAPS, La Rochelle (FR)

( * ) Notice: Subject to any disclaimer, the term of this patent is extended or adjusted under 35 U.S.C. 154(b) by 0 days.

(21) Appl. No.: 14/054,996

(22) Filed: Oct. 16, 2013

(65) Prior Publication Data

US 2014/0037744 A1 Feb. 6, 2014

Related U.S. Application Data

(63) Continuation-in-part of application No. PCT/EP2013/057739, filed on Apr. 12, 2013.

(60) Provisional application No. 61/623,210, filed on Apr. 12, 2012.

(30) Foreign Application Priority Data

Apr. 12, 2012 (EP) .................................. 12 305 434

(51) Int. Cl.
| | | |
|---|---|---|
| *A61K 38/44* | (2006.01) | |
| *A61K 47/36* | (2006.01) | |
| *A61K 8/11* | (2006.01) | |
| *A61K 9/50* | (2006.01) | |
| *A23D 9/00* | (2006.01) | |
| *A23L 1/30* | (2006.01) | |
| *A23L 1/302* | (2006.01) | |
| *A23L 1/304* | (2006.01) | |
| *A23L 1/00* | (2006.01) | |
| *A23L 2/52* | (2006.01) | |
| *A61K 31/375* | (2006.01) | |
| *A23L 1/0534* | (2006.01) | |
| *A23L 1/056* | (2006.01) | |

(52) U.S. Cl.
CPC ................ *A61K 9/5089* (2013.01); *A23D 9/00* (2013.01); *A23L 1/0029* (2013.01); *A23L 1/0061* (2013.01); *A23L 1/056* (2013.01); *A23L 1/0534* (2013.01); *A23L 1/302* (2013.01); *A23L 1/3002* (2013.01); *A23L 1/304* (2013.01); *A23L 1/3006* (2013.01); *A23L 2/52* (2013.01); *A61K 9/5036* (2013.01); *A61K 31/375* (2013.01); *A61K 38/446* (2013.01)

(58) Field of Classification Search
CPC .. A61K 38/446; A61K 9/5036; A61K 9/5089
See application file for complete search history.

(56) References Cited

U.S. PATENT DOCUMENTS

| | | | |
|---|---|---|---|
| 3,714,065 A * | 1/1973 | Kitajima et al. | 427/213.36 |
| 5,780,056 A | 7/1998 | Akamatsu et al. | |
| 2007/0141211 A1 | 6/2007 | Kolar, Jr. et al. | |
| 2009/0004333 A1 | 1/2009 | Nakhasi et al. | |
| 2010/0173002 A1 * | 7/2010 | Yulai et al. | 424/492 |

FOREIGN PATENT DOCUMENTS

| | | |
|---|---|---|
| EP | 1 300 394 A1 | 4/2003 |
| WO | 2010/013250 A2 | 2/2010 |

OTHER PUBLICATIONS

Lee et al., Bioconjugate Chem., 2007, 18, 4-7.*
International Search Report in corresponding Application No. PCT/EP2013/057739, dated May 27, 2013.

* cited by examiner

*Primary Examiner* — Abigail Fisher
(74) *Attorney, Agent, or Firm* — Young & Thompson

(57) ABSTRACT

Disclosed is a microcapsule including a core having an oxidizable active (OA), the outer part of said core being in a solid form, and a water insoluble coating obtained from an encapsulating agent (EA), with the coating surrounding said core. In particular, there is disclosed a microcapsule wherein the EA is water soluble or organic solvent, in particular ethanol, soluble, or a microcapsule wherein said EA is an agent, the water solubility of which is pH-dependent. In particular, the core does not consist in or comprise a metal oxide, and the coating does not comprise a disintegrant, in particular sodium starch glycolate. Also disclosed is a process for preparing the microcapsules.

20 Claims, 6 Drawing Sheets

MICROCAPSULES CONTAINING AN OXIDIZABLE ACTIVE, AND A PROCESS FOR PREPARING THE SAME

FIELD OF THE INVENTION

The present invention relates to microcapsules containing an oxidizable active, undo process for preparing the same.

BACKGROUND OF THE INVENTION

There is an increasing need in the industry, for example in the food, pharmaceutical or cosmetics industry, for protection of active agents from the medium that surrounds said active agents in particular to achieve a better conservation of said active agents.

One of the main issues of encapsulation is to be able to protect drugs from external medium but also to allow the right release or the right access to this drug when needed. This access is very often possible through a quick or controlled release in the medium, due to chosen properties of the encapsulating agent.

This dual aim of protection and release becomes more complex as soon as exchanges between drugs and medium need to be kept out of direct interactions in-between drug and external medium. S. K. Tam and al. have shown (in Vandamme et al *Microencapsulation*; Tec & Doc; 2007; Chapter 11) these issues when the microencapsulation aims to allow therapeutic effects through useful component exchanges, components which are able to cross the microencapsulation barriers while preserving drugs from being in direct contact with other potentially damaging components, if they had entered the microcapsule.

In case of oxidizable drugs, the issue is to be able to get microcapsules which are able to protect these drugs from oxidation, and to protect the external medium from component issued from oxidation of said drugs.

Different kind of encapsulating agents can target this type of protection, but polysaccharides are the most often used. They are mainly used under bead forms containing solutions and cross-linked in salt or cations solutions. Such beads are then stored in wet forms as suspensions particles in solutions.

Chen and al. *Journal of Controlled Release* 2004, 96, 285-300 reported that such beads of polysaccharides can protect bioactive molecules from harsh acidic conditions such as stomach environment. But no works seem to have been made on the use of such a protection of the external medium from oxidizable agents which could decompose media components.

Moreover, the use of such polysaccharides is mainly achieved with cross-linking through dropping of aqueous solutions containing said polysaccharides into aqueous solutions containing salts.

However, the obtained, beads suffer several drawbacks: they are mainly stored in aqueous solution, rendering their handling difficult, their production and their transportation expensive. In addition, said beads cannot be used directly in powder preparation, in particular food powder compositions, or in tablets, in particular for pharmaceutical uses.

No studies have been made on powder microcapsules allowing dry forms of drug protections through process avoiding aqueous solution to create the insoluble external protection of the microcapsule.

SUMMARY OF THE INVENTION

Thus, one aim of the present invention is on the one hand to encapsulate oxidizable active products to protect the media from their action, and on the other hand to implement new processes allowing the manufacture of these microcapsules with no absolute need, to submerge the microcapsules in a cross linking bath of an aqueous salt solution.

Another aim of the present invention is to provide microcapsules able to protect an active from oxidation by a given alimentary, cosmetically or pharmaceutically acceptable medium in which said microcapsules are placed.

Another aim of the present invention is to provide microcapsules able to protect the alimentary, cosmetically or pharmaceutically acceptable medium in which said microcapsules are placed from the active contained in said microcapsules.

Thus, the present invention relates to a microcapsule consisting in or containing:

a core consisting in or comprising an oxidizable active (OA), and a water insoluble coating obtained from an encapsulating agent (EA), said coating surrounding said core.

By microcapsule is meant a particle with a size from 1 μm to a 3 mm, comprising an external coating that isolates an encapsulated core from the external medium.

By core is meant the material inside the microcapsule.

By coating is meant the wall surrounding the core of said microcapsule.

By "water insoluble coating" is meant a coating, the water solubility of which is low enough to prevent said active to be released from the microcapsule, when said microcapsule is placed in an aqueous-based alimentary, cosmetically or pharmaceutically acceptable medium.

The insolubilization of a microcapsule, and thus the fact that said coating prevents said active to be released from said microcapsule is for example determined by the measurement of particle size in water, for instance with a laser particle sizer.

By "prevent said active to be released from the microcapsule" is meant that, when said microcapsule is placed in said medium, the concentration of active in the medium surrounding said microcapsule is below 5% in weight at 25° C., in particular 1% in weight at 25° C.

By "oxidizable active" is meant an active that is capable of being oxidized.

By "active being oxidized" is meant a reducing agent oxidized by having its electrons taken away.

The tendency of an active of having its electrons taken away and thereby be oxidized is in particular measured by its redox potential, as known by those skilled in the art: an active is likely to be oxidized by an element of the external medium if the redox potential of said element is superior to the redox potential of said active.

By "encapsulation agent" is meant a water insoluble agent constituting said water insoluble coating, or a water soluble or organic solvent, in particular ethanol, soluble agent forming said water insoluble coating after a modification of its chemical state.

Two cases can thus be distinguished regarding said water soluble or organic solvent-soluble agent:

the first one corresponds to a water soluble agent forming said water insoluble coating after a modification of its chemical state;

the second one corresponds to a water soluble and organic solvent, in particular ethanol, soluble agent forming said water insoluble coating after a modification of its chemical state.

The term "modification of its chemical state" means in particular a chemical reaction or a pH modification.

The present invention also relates to a microcapsule consisting in or containing:

a core consisting in or comprising an oxidizable active (OA), the outer part of said core being in a solid form, and a water insoluble coating obtained from an encapsulating agent (EA), said coating surrounding said core, with the proviso that:

said core does not consist in or comprise a metal oxide, and said coating does not comprise a disintegrant, in particular sodium starch glycolate.

By "outer part" is meant the part of said core which is in contact with said coating.

By "solid form" is meant a crystalline, semi-crystalline or amorphous state.

In an advantageous embodiment, the present invention relates to a microcapsule, wherein said core is under solid form.

In a particularly advantageous embodiment, the present invention relates to a microcapsule, wherein said core is crystalline. In this case, said oxidizable active is necessarily crystalline.

In another particularly advantageous embodiment, the present invention relates to a microcapsule, wherein said core is crystalline and solid, i.e. without any space or air cavities.

In another particularly advantageous embodiment, the present invention relates to a microcapsule, wherein said core is crystalline and contains at least one space or air cavity.

In another particularly advantageous embodiment, the present invention relates to a microcapsule, wherein said core is crystalline and has a water content less than 10%, in particular less than 6%, by weight.

In another particularly advantageous embodiment, the present invention relates to a microcapsule, wherein said core is under solid form and amorphous.

In another particularly advantageous embodiment, the present invention relates to a microcapsule, wherein said core is amorphous and contains at least one space or air cavity, said core being in particular obtained by spray drying.

In another particularly advantageous embodiment, the present invention relates to a microcapsule, wherein said core is amorphous and has a water content less than 10%, in particular less than 6%, by weight.

In an advantageous embodiment, the present invention relates to a microcapsule, wherein the inner part of said core contains the oxidizable active (OA), said OA being in a liquid form, in particular in an oily form, or in a viscous oil form, or in a pasty form.

In a particularly advantageous embodiment, the present invention relates to a microcapsule, wherein said inner part of said core is a solid comprising the OA in a liquid form, in particular in an oily form, or in a viscous oil form, or in a pasty form.

In an advantageous embodiment, the present invention relates to a microcapsule, wherein said core does not consist in or comprise phospholipids.

In an advantageous embodiment, the present invention relates to a microcapsule consisting in:

a single core consisting in or comprising an oxidizable active (OA) under solid form, and a single water insoluble coating obtained from an encapsulating agent (EA), said coating surrounding said core.

By <<single core>> is meant a core forming a single and continuous volume inside said microcapsule.

By "single coating" is meant that said single core is surrounded by a single wall separating said core from the outside.

In an advantageous embodiment, the present invention relates to a microcapsule, wherein said oxidizable agent does not belong to carotenoids.

In an advantageous embodiment, the present invention relates to a microcapsule wherein the totality of said OA is found in said core.

In an advantageous embodiment, the present invention relates to a microcapsule consisting in or containing:

a core consisting in or comprising an oxidizable active (OA), and a water insoluble coating obtained from an encapsulating agent (EA), said coating surrounding said core, providing said microcapsule is placed in an external medium that do not comprise said OA.

In an advantageous embodiment, the present invention relates to a microcapsule consisting in or containing:

a core consisting in or comprising an oxidizable active (OA), and a water insoluble coating obtained from an encapsulating agent (EA), said coating surrounding said core, providing said microcapsule is placed in an external medium that do not comprise vitamin C or a chemical derivative of vitamin C.

In an advantageous embodiment, the present invention relates to a microcapsule comprising less than 10%, in particular less than 6%, in weight of water.

In an advantageous embodiment, the present invention relates to a microcapsule wherein said EA is water soluble.

By "water soluble EA" is meant an EA that is sufficiently soluble in water to form a clear solution to the naked eye at a concentration of 5% in weight in water at 25° C.

By "water insoluble EA" is meant an EA that is sufficiently insoluble in water to form a turbid solution to the naked eye at a concentration of 1 to 5% in weight in water at 25° C.

In an advantageous embodiment, the present invention relates to a microcapsule wherein said EA is organic solvent, in particular ethanol, soluble.

By "organic solvent, in particular ethanol, soluble EA" is meant an EA that is sufficiently soluble in said solvent, in particular ethanol, to form a clear solution to the naked eye at a concentration of 5% in weight in said solvent at 25° C.

In an advantageous embodiment, the present invention relates to a microcapsule wherein said EA is an agent, the water solubility of which is pH-dependent.

By "an agent, the water solubility of which is pH-dependent" is meant that there is at least one pH value for which said agent is water soluble and at least one pH value for which said agent is water insoluble.

In an advantageous embodiment, the present invention relates to a microcapsule wherein said water insoluble coating results from the reaction of a water soluble EA with means for inducing water insolubility of said EA.

In an advantageous embodiment, the present invention relates to a microcapsule wherein said water insoluble coating results from the reaction of an organic solvent, in particular ethanol, soluble EA with means for inducing water insolubility of said EA.

By "means for inducing water insolubility" is meant any means that modify the chemical state of said water soluble or organic solvent, in particular ethanol, soluble EA, providing a species that is water insoluble in standard reference conditions of temperature and pressure corresponding to a temperature of 25° C. and a pressure of 100 KPa.

In an advantageous embodiment, the present invention relates to a microcapsule wherein said means for inducing water insolubility are an agent chemically reacting with said EA.

Said means react with said water soluble or organic solvent, in particular ethanol, soluble EA, providing a water insoluble species.

In an advantageous embodiment, the present invention relates to a microcapsule wherein said means for inducing water insolubility are an acid, a base, or a buffer.

Said acid, base, of buffer brings the pH from a value for which said EA is water soluble to a value for which said EA is water insoluble.

In an advantageous embodiment, the present invention relates to a microcapsule wherein said means for inducing water insolubility consist in the drying of said EA.

In an advantageous embodiment, the present invention relates to a microcapsule wherein said water insoluble coating is made of a water insoluble EA.

In an advantageous embodiment, the present invention relates to a microcapsule wherein said coating is such that, when said microcapsule is placed in an alimentary, cosmetically or pharmaceutically acceptable medium:
said OA is not degraded by element(s) of said medium, and
said element(s) of the medium is (are) not degraded by said OA.

By "OA not degraded by element(s)", it means that the OA is not oxidized or modified by oxidation, in presence of element(s) of said medium.

Said degradation can be measured by standard analytical method such as HPLC, for example HPLC ascorbic acid dosage when said OA is vitamin C.

By "element(s) of the medium is (are) not degraded by said OA", it means that the element(s) is (are) not directly degraded by said OA, or degraded by product(s) issued from oxidative reactions involving said OA.

The degradation of a given medium is measured according to criteria known by those skilled in the art.

For example, when said OA is ascorbic acid, a medium containing iron salts preferably under $Fe^{2+}$ salt, would lead to the formation in the medium of iron ascorbate detectable with its specific black color.

In an advantageous embodiment, the present invention relates to a microcapsule wherein said coating is such that, when said microcapsule is placed in a fermented food composition, in particular in a fermented vegetal milk composition:
said OA is not degraded by element(s) of said composition, and
said element(s) of the composition is (are) not degraded by said OA,
provided said composition is not a fermented dairy food composition.

In an advantageous embodiment, the present invention relates to a microcapsule wherein said coating is such that, when said microcapsule is placed in an unfermented food composition, in particular in an unfermented dairy or an unfermented vegetal milk composition:
said OA is not degraded by element(s) of said composition, and
said element(s) of the composition is (are) not degraded by said OA.

In an advantageous embodiment, the present invention relates to a microcapsule wherein said coating is such that, when said microcapsule is placed in a alimentary, cosmetically or pharmaceutically acceptable medium comprising globular proteins, in particular a medium comprising or consisting in an unfermented dairy or an unfermented vegetal milk composition and a medium comprising or consisting in a fermented vegetal milk compositions:
said OA is not degraded by element(s) of said medium, and
said element(s) of the medium is (are) not degraded by said OA,
provided said medium do not consist in or comprise a fermented dairy food composition.

In an advantageous embodiment, the present invention relates to a microcapsule wherein said coating is such that when said microcapsule is placed in a alimentary, cosmetically or pharmaceutically acceptable medium comprising $Ca^{2+}$ cations, in particular a medium comprising or consisting in an unfermented dairy or an unfermented vegetal milk composition and a medium comprising or consisting in a fermented vegetal milk compositions:
said OA is not degraded by element(s) of said medium, and
said element(s) of the medium is (are) not degraded by said OA,
provided said medium do not consist in or comprise a fermented dairy food composition.

In an advantageous embodiment, the present invention relates to a microcapsule wherein the mass of said coating is within the range from 3 to 50%, preferably from 4 to 12%, more preferably from 5 to 8%, of the total mass of said microcapsule.

In an advantageous embodiment, the present invention relates to a microcapsule wherein said microcapsule size is in range from 1 µm to 3 mm, preferably from 20 to 500 µm, more preferably from 50 to 200 µm.

In an advantageous embodiment, the present invention relates to a microcapsule wherein said OA is in a crystalline state.

By "crystalline state" is meant a state wherein OA molecules are arranged in an orderly, repeating pattern.

Examples of OA in a crystalline state are commercial available crystallized vitamins, such as crystallized vitamin C.

In an advantageous embodiment, the present invention relates to a microcapsule wherein said core consists in or comprises an OA in a crystalline state and at least one additional element selected among drying agents, antioxidant agents, filmogen agents and emulsifying agents.

Drying agents are for example starch, maltodextrin, proteins in particular caseinates, gelatin, vegetable proteins in particular soya, wheat and pea proteins, gums in particular acacia gum as well known by those skilled in the art.

Examples of antioxidant agents are sodium ascorbate, ascorbyl palmitate, vitamin E, and tocopherol acetate.

Filmogen agents are for example proteins in particular caseinate, gums, cellulose derivatives as well known by those skilled in the art.

Examples of emulsifying agents are lecithin, proteins, hydrolyzed proteins, modified starch as well known by those skilled in the art.

In an advantageous embodiment, the present invention relates to a microcapsule wherein said OA is in an amorphous state.

By "amorphous state" is meant a state wherein OA molecules are not arranged in an orderly, repeating pattern.

Compounds in an amorphous state are for instance described in Hancock et al. *Journal of Pharmaceutical Sciences* 1997, 86(1), pages 1-12.

Examples of OA in an amorphous state are OA amorphous solids obtained by spray-drying, under condition known by those skilled in the art: spray drying is known to produce predominately amorphous material from a homogenous solution, due to the almost instantaneous transition between liquid and solid phases.

It is noted that a microcapsule of the invention, wherein said OA is optionally in a crystalline or an amorphous state, can let small molecules such as protons and water pass through its coating when said microcapsule is placed in water or in an aqueous medium.

In an advantageous embodiment, the present invention relates to a microcapsule wherein said OA is water soluble.

When water from an external medium consisting in water or an aqueous medium passes through said coating in an amount enough to dissolve said water soluble OA, a microcapsule consisting in or containing a aqueous solution of said OA and said water insoluble coating is obtained. Such a microcapsule allows a better bioavailability compared to particles where said OA is in a solid form, as said water soluble OA is already dissolved in water.

In an advantageous embodiment, the present invention relates to a microcapsule wherein said core consists in or comprises an OA in an amorphous state and at least one additional element selected among drying agents, antioxidant agents, filmogen agents and emulsifying agents.

In an advantageous embodiment, the present invention relates to a microcapsule wherein said core consists in or comprises an OA and water, the core being a solution, a liquid suspension or an emulsion of said OA in water.

In an advantageous embodiment, the present invention relates to a microcapsule consisting in or containing:

a core consisting in or comprising an OA, water and at least one additional element selected, among drying agents, antioxidant agents, filmogen agents and emulsifying agents, the core being a solution, a liquid suspension or an emulsion of said OA and said at least one additional elements in water, and an insoluble coating of a EA, said coating surrounding said core.

In an advantageous embodiment, the present invention relates to a microcapsule wherein said water soluble EA is selected from alginates of monovalent cations, in particular $Na^+$ alginates and $K^+$ alginates.

Alginates enable said OA not to be released in some external media but to be released from said microcapsules only into a specific medium, such as in the gastrointestinal tract, wherein release of said OA is desired, in a controlled manner.

In an advantageous embodiment, the present invention relates to a microcapsule wherein said means for inducing water insolubility are a salt wherein the cation is a divalent metallic cation, in particular $Ca^{2+}$ or $Mg^{2+}$, said salt being in particular $CaCl_2$ or $MgCl_2$.

In an advantageous embodiment, the present invention relates to a microcapsule wherein said water insoluble coating is selected from alginates of divalent cations, in particular $Ca^{2+}$ alginates and $Mg^{2+}$ alginates.

In an advantageous embodiment, the present invention relates to a microcapsule wherein said EA is water soluble and selected from alginates of monovalent cations, in particular $Na^+$ alginates and $K^+$ alginates, and wherein said means for inducing water insolubility are a salt wherein the cation is a divalent metallic cation, in particular $Ca^{2+}$ or $Mg^{2+}$, said salt being in particular $CaCl_2$ or $MgCl_2$.

In an advantageous embodiment, the present invention relates to a microcapsule wherein no divalent ion, in particular no $Ca^{2+}$, is present in said core.

In an advantageous embodiment, the present invention relates to a microcapsule wherein said EA is a resin, the water solubility of which is pH-dependent, in particular Lac gum.

In an advantageous embodiment, the present invention relates to a microcapsule wherein said EA is a resin that is water soluble in basic conditions and water insoluble in acidic conditions, in particular shellac gum.

In an advantageous embodiment, the present invention relates to a microcapsule wherein said EA is a resin that is soluble in an organic solvent, in particular in ethanol.

In an advantageous embodiment, the present invention relates to a microcapsule wherein said means for inducing water insolubility are an acid, in particular an ascorbic acid.

In an advantageous embodiment, the present invention relates to a microcapsule wherein said EA is water insoluble and selected from cellulose polymers, in particular ethylcellulose.

In an advantageous embodiment, the present invention relates to a microcapsule wherein said EA is a cellulose polymer that is soluble in an organic solvent, in particular in ethanol.

In an advantageous embodiment, the present invention relates to a microcapsule wherein said water soluble EA is lac gum, said means for inducing water insolubility consisting in particular in the drying of said lac gum.

By "lac gum" is meant a purified product of the natural resinous secretion of the insect Kerria Lacca, which is in particular found in India and Thailand.

By "drying of said lac gum" is meant applying a temperature that is high enough to evaporate the solvent used for the dissolution of the Lac gum, for example from about 30° C. to about 70° C. when the solvent is aqueous, or from about 10° C. to about 40° C. when the solvent is an organic solvent, in particular ethanol.

In an advantageous embodiment, the present invention relates to a microcapsule wherein said water soluble or organic solvent, in particular ethanol, soluble EA is lac gum, and said means for inducing water insolubility are an acid, in particular ascorbic acid, citric acid, acetic acid or hydrochloric acid.

In an advantageous embodiment, the present invention relates to a microcapsule wherein said OA is selected from the group comprising vitamin C, vitamin B5, vitamin B6, vitamin B8, vitamin B9, vitamin A, vitamin D3, vitamin K and vitamin E.

In an advantageous embodiment, the present invention relates to a microcapsule wherein said OA is vitamin C, in particular natural vitamin C, synthetic vitamin C, or salts of L-ascorbic acid, more particularly sodium L-ascorbate, calcium L-ascorbate and iron L-ascorbate.

In an advantageous embodiment, the present invention relates to a microcapsule wherein said OA comprises vitamin C, said OA being in particular a fruit juice comprising vitamin C, in particular orange juice, kiwi juice, cranberry juice or acerola juice, said fruit juice being optionally concentrated or dried.

In an advantageous embodiment, the present invention relates to a microcapsule wherein said OA comprises vitamin C, said OA being in particular a fruit juice comprising vitamin C, in particular orange juice, kiwi juice, cranberry juice, acerola juice or goji juice, said fruit juice being optionally concentrated or dried.

In an advantageous embodiment, the present invention relates to a microcapsule wherein said OA is vitamin C or comprises vitamin C and wherein said EA is water soluble and selected from alginates of monovalent cations, in particular $Na^+$ alginates and $K^+$ alginates.

In an advantageous embodiment, the present invention relates to a microcapsule wherein said OA is vitamin C or comprised vitamin C, wherein said EA is water soluble and selected from alginates of monovalent cations, in particular $Na^+$ alginates and $K^+$ alginates, and wherein said means for inducing water insolubility are a salt wherein the cation is a divalent metallic cation, in particular $Ca^{2+}$ or $Mg^{2+}$, said salt being in particular $CaCl_2$ or $MgCl_2$.

In an advantageous embodiment, the present invention relates to a microcapsule wherein said OA is selected from the group comprising dihydroxyacetone (DHA), enriched in omega 3 or omega 6 oil, and oxidizable enzymes, in particular superoxydismutase (SOD).

In an advantageous embodiment, the present invention relates to a microcapsule wherein said OA is superoxydismutase (SOD), in particular freeze-dried SOD or spray-dried SOD.

In an advantageous embodiment, the present invention relates to a microcapsule wherein said OA is SOD, said EA is water soluble or organic solvent, in particular ethanol, soluble, said water soluble or organic solvent-soluble EA being lac gum, and said means for inducing water insolubility consist in the drying of said lac gum.

In an advantageous embodiment, the present invention relates to a microcapsule wherein said OA is SOD, said water soluble or organic solvent, in particular ethanol, soluble EA is lac gum, and said means for inducing water insolubility are an acid, in particular ascorbic acid, citric acid, acetic acid or hydrochloric acid.

In an advantageous embodiment, the present invention relates to a microcapsule wherein said OA is SOD, said EA is water soluble, said water soluble EA being selected from alginates of monovalent cations, in particular $Na^+$ alginates and $K^+$ alginates, and said means for inducing water insolubility are a salt wherein the cation is a divalent metallic cation, in particular $Ca^{2+}$ or $Mg^{2+}$, said salt being in particular $CaCl_2$ or $MgCl_3$.

In an advantageous embodiment, the present invention relates to a microcapsule wherein said OA is SOD and said EA is water insoluble.

In another aspect, the present invention relates to a process of preparation of microcapsules described above, comprising the following steps:
  a spray-drying a liquid mixture consisting in or comprising:
    said OA;
    optionally said EA;
    optionally at least one additional element selected among drying agents, antioxidant agents, filmogen agents and emulsifying agents;
to obtain particles consisting in said OA, or particles comprising said OA, and said EA and/or at least one additional element,
  spraying on said particles an insoluble EA or means for inducing water insolubility of EA comprised in said particle, to obtain microcapsules with a water insoluble coating, said water insoluble coating surrounding a core consisting in said OA, or comprising said OA, and said EA and/or at least one additional element.

It is noted that said OA is, in said obtained microcapsule, predominantly in an amorphous state as spray drying is known to produce predominantly amorphous material from a homogenous solution, due to the almost instantaneous transition between liquid and solid phases.

The obtained microcapsules comprising said OA predominantly in an amorphous state have typically a size comprised from 1 μm to 1000 μm, preferably from 20 μm to 500 μm, and more preferably from 50 to 200 μm.

The present invention also relates to a process of preparation of microcapsules comprising the following steps:
  a spray-drying a liquid mixture consisting in or comprising:
    said OA;
    optionally said EA;
    optionally at least one additional element selected among drying agents, antioxidant agents, filmogen agents and emulsifying agents;
to obtain particles consisting in said OA, or particles comprising said OA, and said EA and/or at least one additional element, the outer part of said particles being in a solid form,
  spraying on said particles an insoluble EA or means for inducing water insolubility of EA comprised in said particle, to obtain microcapsules with a water insoluble coating, said water insoluble coating surrounding a core consisting in said OA, or comprising said OA, and said EA and/or at least one additional element,
with the proviso that:
    said core does not consist in or comprise a metal oxide, and
    said coating does not comprise a disintegrant, in particular sodium starch glycolate.

In an advantageous embodiment, the present invention relates to a process of preparation of microcapsules described above, comprising the following steps:
  a spray-drying a liquid mixture consisting in or comprising:
    said OA;
    optionally said EA;
    optionally at least one additional element selected among drying agents, antioxidant agents, filmogen agents and emulsifying agents;
to obtain particles consisting in said OA in an amorphous state, or particles comprising said OA in an amorphous state, and said EA and/or at least one additional element,
  spraying on said particles an insoluble EA or means for inducing water insolubility of EA comprised in said particle, to obtain microcapsules with a water insoluble coating, said water insoluble coating surrounding a core consisting in said OA in an amorphous state, or comprising said OA in an amorphous state, and said EA and/or at least one additional element.

In an advantageous embodiment, the present invention relates to a process comprising, after said spray-drying and spraying steps, a step of drying said microcapsules to obtain dried microcapsules.

In an advantageous embodiment, the present invention relates to a process wherein said spray-drying step is done in a spray-dryer and said spraying step and drying step are done in a coating device by spray, in particular a coating device by spray comprising a fluidized bed.

Examples of spray-dryer wherein the spray-drying step can be performed are single effect spray-drying towers, toll form spray-drying towers, belt dryer and multiple effect spray-drying towers with internal or external fluid bed.

Examples of coating device by spray wherein the spraying step can be performed are fluidized beds, top spray, tangential spray, bottom spray or wurster devices, batch process devices or continuous devices as horizontal fluid bed or multicellular fluid bed; these devices being as described in Vandamme et al *Microencapsulation*; Tec & Doc; 2007; Chapter 10.

In an advantageous embodiment, the present invention relates to a process wherein said spray-drying step, spraying step and drying step are done in the same spray-dryer.

Interestingly, the Inventors have found that the microcapsules, obtained by a process wherein said spray-drying step, spraying step and drying step are done in the same spray-dryer, surprisingly protect said OA from oxidation by a given alimentary, cosmetically or pharmaceutically acceptable medium in which said microcapsules are placed, and said medium from said OA.

Examples of spray-dryer wherein the spray-drying step and the spraying step can be performed are single effect spray-drying towers, toll form spray-drying towers, belt dryer and multiple effect spray-drying towers with internal or external fluid bed.

In an advantageous embodiment, the present invention relates to a process of preparation of microcapsules described above, comprising the following steps:

spray-drying a liquid mixture consisting in or comprising:
   said OA;
   optionally said EA;
   optionally at least one additional element selected among drying agents, antioxidant agents, filmogen agents and emulsifying agents;
to obtain particles consisting in said OA in an amorphous state, or particles comprising said OA in an amorphous state, and said EA and/or at least one additional element,
spraying on said particles an insoluble EA or means for inducing water insolubility of EA comprised in said particle, to obtain microcapsules with a water insoluble coating, said water insoluble coating surrounding a core consisting in said OA in an amorphous state, or comprising said OA in an amorphous state, and said EA and/or at least one additional element,
drying said microcapsules to obtain dried microcapsules, said spray-drying step, spraying step and drying step being done in the same spray-dryer.

In an advantageous embodiment, the present invention relates to a process wherein said means for inducing water insolubility are an agent chemically reacting with said EA.

In an advantageous embodiment, the present invention relates to a process wherein said means for inducing water insolubility are an acid, a base, or a buffer.

In an advantageous embodiment, the present invention relates to a process comprising the following steps:
spray-drying a liquid mixture consisting in or comprising:
   said OA;
   optionally at least one additional element selected among drying agents, antioxidant agents, filmogen agents and emulsifying agents;
to obtain particles consisting in said OA, or particles comprising said OA and said at least one additional element.
spraying on said particles a water insoluble EA, to obtain microcapsules with a water insoluble coating, said water insoluble coating surrounding a core consisting in said OA, or comprising said OA and said at least one additional element.

In an advantageous embodiment, the present invention relates to a process comprising the following steps:
a spray-drying a liquid mixture consisting in or comprising:
   said OA;
   a water soluble EA;
   optionally at least one additional element selected among drying agents, antioxidant agents, filmogen agents and emulsifying agents;
to obtain particles comprising said OA, said EA and optionally said at least one additional element,
a spraying on said particles means for inducing water insolubility of EA comprised in said particle, to obtain microcapsules with a water insoluble coating, said water insoluble coating surrounding a core comprising said OA, said EA and optionally at least one additional element.

Interestingly, the Inventors have found that the fact of inducing water insolubility of EA by spraying said means, in particular in aqueous solution, on solid dried particles (comprising said OA and said EA) obtained by spray-drying, surprisingly forms a protective coating that has the ability to protect said OA from oxidation by a given alimentary, cosmetically or pharmaceutically acceptable medium in which said microcapsules are placed, and said medium from said OA.

Said process of the invention, wherein water insolubility of EA is induced by spraying means on solid dried particles is a spray-drying process with respect to said particles, which are dried before said spraying.

In an advantageous embodiment, the present invention relates to a process comprising the following steps:
a spray-drying a liquid mixture consisting in or comprising:
   said OA;
   alginate of monovalent cation, in particular $Na^+$ alginate and $K^+$ alginate;
   optionally at least one additional element selected among drying agents, antioxidant agents, filmogen agents and emulsifying agents;
to obtain particles comprising said OA, said alginate and optionally said at least one additional element,
a spraying on said particles means for inducing water insolubility of alginate comprised in said particle, to obtain microcapsules with a water insoluble coating, said water insoluble coating surrounding a core comprising said OA, said EA and optionally at least one additional element.

In an advantageous embodiment, the present invention relates to a process comprising the following steps:
a spray-drying a liquid mixture consisting in or comprising:
   said OA;
   alginate of monovalent cation, in particular $Na^+$ alginate and $K^+$ alginate;
   optionally at least one additional element selected among drying agents, antioxidant agents, filmogen agents and emulsifying agents;
to obtain particles comprising said OA, said alginate and optionally said at least one additional element,
spraying on said particles an aqueous solution of a salt wherein the cation is a divalent metallic cation, in particular $Ca^{2+}$ or $Mg^{2+}$, said salt being in particular $CaCl_2$ or $MgCl_2$, to obtain microcapsules with a water insoluble coating, said water insoluble coating surrounding a core comprising said OA, said EA and optionally at least one additional element;
a drying said microcapsules to obtain dried microcapsules.

In an advantageous embodiment, the present invention relates to a process wherein said liquid mixture is a homogenous aqueous solution.

The liquid mixture is a homogenous aqueous solution when said OA, said EA and, provided an additional element is present in said mixture, said additional element are water soluble.

When the liquid mixture is a homogenous aqueous solution, the size of the obtained microcapsules are driven by the parameters of spray-drying, and not by the characteristics of said water soluble OA.

The microcapsules obtained have typically a size comprised from 1 μm to 1000 μm, preferably from 20 μm to 500 μm, and more preferably from 50 to 200 μm.

In an advantageous embodiment, the present invention relates to a process wherein said liquid mixture is a solid-in-liquid suspension or an emulsion.

In an advantageous embodiment, the present invention relates to a process wherein said liquid mixture is a homogenous aqueous solution consisting in or comprising said OA.

In an advantageous embodiment, the present invention relates to a process wherein said liquid mixture is a homogenous aqueous solution consisting in or comprising said OA and at least one additional element selected among drying agents, antioxidant agents, filmogen agents and emulsifying agents.

In an advantageous embodiment, the present invention relates to a process wherein said liquid mixture is a homogenous aqueous solution consisting in or comprising said OA and said water soluble EA.

In an advantageous embodiment, the present invention relates to a process wherein said liquid mixture is a homogenous aqueous solution consisting in or comprising said OA, said water soluble EA, and at least one additional element selected among drying agents, antioxidant agents, filmogen agents and emulsifying agents.

In another aspect, the present invention relates to a process comprising a step of spraying on particles consisting in said OA, or particles comprising said OA, and said EA and/or at least one additional element selected among drying agents, antioxidant agents, filmogen agents and emulsifying agents, an insoluble EA or means for inducing water insolubility of EA comprised in said particle, to obtain microcapsules with a water insoluble coating, said water insoluble coating surrounding a core consisting in said OA, or comprising said OA, and said EA and/or at least one additional element.

In an advantageous embodiment, the present invention relates to a process comprising, after said spraying step, a step of drying said microcapsules to obtain dried microcapsules.

In an advantageous embodiment, the present invention relates to a process wherein said means for inducing water insolubility are an agent chemically reacting with said EA.

In an advantageous embodiment, the present invention relates to a process wherein said means for inducing water insolubility are an acid, a base, or a buffer.

In an advantageous embodiment, the present invention relates to a process comprising a step of spraying on particles consisting in said OA, or particles comprising said OA and at least one additional element selected among drying agents, antioxidant agents, filmogen agents and emulsifying agents, a water insoluble coating to obtain microcapsules with a water insoluble coating, said water insoluble coating surrounding a core consisting in said OA, or comprising said OA, and said at least one additional element.

In an advantageous embodiment, the present invention relates to a process comprising a step of spraying in a device on particles comprising:
said OA,
a water soluble EA, and
optionally at least one additional element selected among drying agents, antioxidant agents, filmogen agents and emulsifying agents,
means for inducing water insolubility of EA comprised in said particle, to obtain microcapsules with a water insoluble coating, said water insoluble coating surrounding a core comprising said OA, and said EA and/or at least one additional element.

Interestingly, the Inventors have found that the fact of inducing water insolubility of EA by spraying said means, in particular in aqueous solution, on solid dried particles (comprising said OA and said EA), for example obtained by spray-drying, surprisingly forms a protective coating that has the ability to protect said OA from oxidation by a given alimentary, cosmetically or pharmaceutically acceptable medium in which said microcapsules are placed, and said medium from said OA.

Examples of device wherein the spraying step can be performed are fluidized beds, top spray, tangential spray, bottom spray or wurster devices, batch process devices or continuous devices as horizontal fluid bed or multicellular fluid bed; these devices being as described in Vandamme et al *Microencapsulation*; Tec & Doc; 2007; Chapter 10.

Said process of the invention, wherein water insolubility of EA is induced by spraying means on solid dried particles is a spray-drying process with respect to said particles, which are dried before said spraying.

Two cases can be distinguished:
the first one occurs when means for inducing water insolubility involves all the EA comprised in said particles; in this case, microcapsules with a core consisting in said OA, or comprising said OA, and optionally at least one additional element, are obtained;
the second one occurs when means for inducing water insolubility involves only a part of the EA comprised in said particles, in particular EA present on or near the surface of said particles; in that case, microcapsules with a core comprising said OA, said EA and optionally at least one additional element, are obtained.

The nature of the means for inducing water insolubility, the mass of EA in respect of the total mass of said microcapsule, and the distribution of EA in said particles are factors that can lead to the first or the second case.

In an advantageous embodiment, the present invention relates to a process comprising a step of spraying on particles comprising:
said OA,
alginate of monovalent cation, in particular $Na^+$ alginate and $K^+$ alginate, and
optionally at least one additional element selected among drying agents, antioxidant agents, filmogen agents and emulsifying agents,
means for inducing water insolubility of alginate comprised in said particle, to obtain microcapsules with a water insoluble coating, said water insoluble coating surrounding a core comprising said OA, and said alginate and/or at least one additional element.

In an advantageous embodiment, the present invention relates to a process comprising a step of spraying on particles comprising:
said OA,
alginate of monovalent cation, in particular $Na^+$ alginate and $K^+$ alginate, and
optionally at least one additional element selected among drying agents, antioxidant agents, filmogen agents and emulsifying agents.
an aqueous solution of a salt wherein the cation is a divalent metallic cation, in particular $Ca^{2+}$ or $Mg^{2+}$, said salt being in particular $CaCl_2$ or $MgCl_2$, to obtain microcapsules with a water insoluble coating, said water insoluble coating surrounding a core comprising said OA, and said alginate and/or at least one additional element.

In an advantageous embodiment, the present invention relates to a process comprising a step of spraying on particles comprising:
said OA,
lac gum, and
optionally at least one additional element selected among drying agents, antioxidant agents, filmogen agents and emulsifying agents,
means for inducing water insolubility of lac gum comprised in said particle, to obtain microcapsules with a water insoluble coating, said water insoluble coating surrounding a core comprising said OA and/or at least one additional element.

Said particles comprising:
said OA,
lac gum, and optionally at least one additional element selected among drying agents, antioxidant agents, filmogen agents and emulsifying agents,
are for example obtained, by spraying lac gum, said lac gum being in particular dissolved in water or ethanol, on particles consisting in said OA or comprising said OA and at least one additional element selected among drying agents, antioxidant agents, filmogen agents and emulsifying agents.

In an advantageous embodiment, the present invention relates to a process comprising a step of spraying on particles comprising:
said OA,
lac gum, and
optionally at least one additional element selected among drying agents, antioxidant agents, filmogen agents and emulsifying agents,
an aqueous solution of an acid, in particular ascorbic acid, citric acid, acetic acid or hydrochloric acid, to obtain microcapsules with a water insoluble coating, said water insoluble coating surrounding a core comprising said OA and/or at least one additional element.

In an advantageous embodiment, the present invention relates to a process comprising a step of spraying on particles comprising:
said OA,
lac gum, and
optionally at least one additional element selected, among drying agents, antioxidant agents, filmogen agents and emulsifying agents,
an aqueous solution of an acid, in particular ascorbic acid, citric acid, acetic acid or hydrochloric acid, to obtain microcapsules with a water insoluble coating, said water insoluble coating surrounding a core comprising said OA and/or at least one additional element,
said OA being superoxydismutase (SOD), in particular freeze-dried SOD or spray-dried SOD.

In an advantageous embodiment, the present invention relates to a process wherein said particles are obtained by coating said OA in a solid state with said water soluble EA and optionally at least one additional element selected among drying agents, antioxidant agents, filmogen agents and emulsifying agents.

In an advantageous embodiment, the present invention relates to a process wherein said particles are obtained by coating said OA in a crystalline state with said water soluble EA and optionally at least one additional element selected among drying agents, antioxidant agents, filmogen agents and emulsifying agents.

Thus, the microcapsules obtained after spraying on said particles means for inducing water insolubility of said EA comprise a core consisting in or comprising OA in a crystalline state.

It is noted that the size of microcapsules is driven by the size of OA particles in crystalline state.

For example, the size of microcapsules obtained from vitamin C particles having a size comprised from 20 to 200 µm is comprised from 20 to 350 µm.

In an advantageous embodiment, the present invention relates to a process wherein said particles are obtained by co-spraying a homogenous aqueous solution comprising:
a said water soluble EA,
optionally at least one additional element selected among drying agents, antioxidant agents, filmogen agents and emulsifying agents;
and said OA in a solid state.

By co-spraying is meant that said homogenous aqueous solution and said OA in a solid state are sprayed jointly in such a manner that the sprayed homogenous aqueous solution films the particles of OA in a solid state to give particles that are totally filmed by the EA.

In an advantageous embodiment, co-spraying is performed with two separate means of pulverization, in particular two separate nozzles.

In an advantageous embodiment, co-spraying is performed with two combined means of pulverization, in particular a trifluid nozzle.

In an advantageous embodiment, the present invention relates to a process wherein said particles are obtained by co-spraying a homogenous aqueous solution comprising:
said water soluble EA,
optionally at least one additional element selected among drying agents, antioxidant agents, filmogen agents and emulsifying agents;
and said OA in a crystalline state.

Thus, the microcapsules obtained after spraying on said particles means for inducing water insolubility of said EA comprise a core consisting in or comprising OA in a crystalline state.

It is noted that the size of microcapsules is driven by the size of OA particles in crystalline state.

For example, the size of microcapsules obtained from vitamin C particles having a size comprised from 20 to 200 µm is comprised from 20 to 350 µm.

In an advantageous embodiment, the present invention relates to a process wherein said particles are obtained by co-spraying a homogenous aqueous solution comprising said water soluble EA and said OA in a solid state.

In an advantageous embodiment, the present invention relates to a process wherein said particles are obtained by co-spraying in a spray-dryer a homogenous aqueous solution comprising:
said water soluble EA;
at least one additional element selected among drying agents, antioxidant agents, filmogen agents and emulsifying agents;
and said OA in a solid state.

In an advantageous embodiment, the present invention relates to a process wherein particles are obtained in a spray-dryer.

In an advantageous embodiment, the present invention relates to a process wherein said spraying of said means for inducing water insolubility of EA is performed in the spray-dryer used to obtain said particles.

Examples of spray-dryer wherein the spray-drying step and the spraying step can be performed are single effect spray-drying towers, toll form spray-drying towers, belt dryer and multiple effect spray-drying towers with internal or external fluid bed.

Interestingly, the Inventors have found that the microcapsules, obtained by a process wherein said spraying of said agent is performed in the same spray-dryer as the one used to obtain said particles, in a single step of obtaining particles by spray-drying and spraying them with said agent, surprisingly protect said OA from oxidation by a given alimentary, cosmetically or pharmaceutically acceptable medium in which said microcapsules are placed, and said medium from said OA.

In an advantageous embodiment, the present invention relates to a process comprising the following steps:
co-spraying in a spray-dryer a homogenous aqueous solution comprising:
a said water soluble EA, optionally at least one additional element selected among drying agents, antioxidant agents, filmogen agents and emulsifying agents;

and said OA in a crystalline state, to obtain particles comprising:
- said OA in a crystalline state,
- said water soluble EA,
- optionally at least one additional element selected among drying agents, antioxidant agents, filmogen agents and emulsifying agents,
- spraying in a device on said particles means for inducing water insolubility of EA comprised in said particles, to obtain microcapsules with a water insoluble coating, said water insoluble coating surrounding a core comprising said OA in a crystalline state, and said EA and/or at least one additional element.

In an advantageous embodiment, the present invention relates to a process comprising the following steps:
co-spraying in a spray-dryer a homogenous aqueous solution comprising:
- a said water soluble EA,
- optionally at least one additional element selected among drying agents, antioxidant agents, filmogen agents and emulsifying agents;

and said OA in a crystalline state, to obtain particles comprising:
- said OA in a crystalline state,
- said water soluble EA,
- optionally at least one additional element selected among drying agents, antioxidant agents, filmogen agents and emulsifying agents,
- spraying in the same spray-dryer on said particles means for inducing water insolubility of EA comprised in said particles, to obtain microcapsules with a water insoluble coating, said water insoluble coating surrounding a core comprising said OA in a crystalline state, and said EA and/or at least one additional element.

In an advantageous embodiment, the present invention relates to a process comprising the following steps:
co-spraying in a spray-dryer a homogenous aqueous solution comprising:
- alginate of monovalent cation, in particular $Na^+$ alginate and $K^+$ alginate, and
- optionally at least one additional element selected among drying agents, antioxidant agents, filmogen agents and emulsifying agents;

and said OA in a solid state, to obtain particles comprising:
- said OA,
- alginate of monovalent cation, in particular $Na^+$ alginate and $K^+$ alginate, and optionally at least one additional element selected among drying agents, antioxidant agents, filmogen agents and emulsifying agents,
- spraying in a device on said particles an aqueous solution of a salt wherein the cation is a divalent metallic cation, in particular $Ca^{2+}$ or $Mg^{2+}$, said salt being in particular $CaCl_2$ or $MgCl_2$, to obtain microcapsules with a water insoluble coating, said water insoluble coating surrounding a core comprising said OA, and said alginate and/or at least one additional element,
- a drying said microcapsules to obtain dried microcapsules.

In an advantageous embodiment, the present invention relates to a process comprising the following steps:
co-spraying in a spray-dryer a homogenous aqueous solution comprising:
- alginate of monovalent cation, in particular $Na^+$ alginate and $K^+$ alginate, and optionally at least one additional element selected among drying agents, antioxidant agents, filmogen agents and emulsifying agents;

and said OA in a solid state, to obtain particles comprising:
- said OA,
- alginate of monovalent cation, in particular $Na^+$ alginate and $K^+$ alginate, and optionally at least one additional element selected among drying agents, antioxidant agents, filmogen agents and emulsifying agents,
- spraying in the same spray-dryer on said particles an aqueous solution of a salt wherein the cation is a divalent metallic cation, in particular $Ca^{2+}$ or $Mg^{2+}$, said salt being in particular $CaCl_2$ or $MgCl_2$, to obtain microcapsules with a water insoluble coating, said water insoluble coating surrounding a core comprising said OA, and said alginate and/or at least one additional element,
- a drying said microcapsules to obtain dried microcapsules.

In an advantageous embodiment, the present invention relates to a process comprising a step of co-spraying in a spray-dryer:
a liquid mixture consisting in or comprising:
- said OA;
- a water soluble EA;
- optionally at least one additional element selected among drying agents, antioxidant agents, filmogen agents and emulsifying agents;

and
means for inducing water insolubility of said EA,
to obtain microcapsules with a water insoluble coating, said water insoluble coating surrounding a core comprising said OA, said EA and optionally at least one additional element.

By co-spraying is meant that said liquid mixture and said means for inducing water insolubility of said EA are sprayed jointly in such a manner that the sprayed means for inducing water insolubility film particles of OA and optionally at least one additional element.

In an advantageous embodiment, co-spraying is performed with two separate means of pulverization, in particular two separate nozzles.

In an advantageous embodiment, co-spraying is performed with two combined means of pulverization, in particular a trifluid nozzle.

In another aspect, the present invention relates to a process comprising the following steps:
spraying, on particles consisting in said OA, or particles comprising said OA and at least one additional element selected among drying agents, antioxidant agents, filmogen agents and emulsifying agents, a water soluble EA to obtain particles surrounded by said EA;

drying said particles surrounded by said EA, to obtain microcapsules with a water insoluble coating, said water insoluble coating surrounding a core comprising said OA, and optionally at least one additional element, said water soluble EA being in particular lac gum, said lac gum being in particular dissolved in water or ethanol.

In an advantageous embodiment, the present invention relates to a process comprising the following steps:
spraying, on particles consisting in said OA, or particles comprising said OA and at least one additional element selected among drying agents, antioxidant agents, filmogen agents and emulsifying agents, a water soluble or organic solvent, in particular ethanol, soluble EA to obtain particles surrounded by said EA;

drying said particles surrounded by said EA, to obtain microcapsules with a water insoluble coating, said water insoluble coating surrounding a core comprising said OA, and optionally at least one additional element, said OA being superoxydismutase (SOD), in particular freeze-dried SOD or spray-dried SOD, said water soluble or organic solvent-soluble EA being in particular lac gum, said lac gum being in particular dissolved in water or ethanol.

In an advantageous embodiment, the present invention relates to a process wherein said spraying step and drying step are done in a spray-dryer.

In an advantageous embodiment, the present invention relates to a process wherein said spraying step and drying step are done in a coating device by spray, in particular a coating device by spray comprising a fluidized bed.

Examples of device wherein the spraying step can be performed are fluidized beds, top spray, tangential spray, bottom spray or wurster devices, batch process devices or continuous devices as horizontal fluid bed or multicellular fluid bed; these devices being as described in Vandamme et al Microencapsulation; Tec & Doc; 2007; Chapter 10.

In an advantageous embodiment, the present invention relates to a process comprising the following steps:
    spray-drying a liquid mixture consisting in or comprising:
        said OA;
        optionally at least one additional element selected among drying agents, antioxidant agents, filmogen agents and emulsifying agents;
to obtain spray-dried particles consisting in said OA, or particles comprising said OA and at least one additional element,
    a spraying on said particles a water soluble or organic solvent, in particular ethanol, soluble EA, to obtain particles surrounded by said EA;
    drying said particles surrounded by said EA, to obtain microcapsules with a water insoluble coating, said water insoluble coating surrounding a core comprising said OA, and optionally at least one additional element,
said water soluble or organic solvent-soluble EA being in particular lac gum, said lac gum being in particular dissolved in water or ethanol.

In an advantageous embodiment, the present invention relates to a process comprising the following steps:
    spray-drying a liquid mixture consisting in or comprising:
        said OA;
        optionally at least one additional element selected among drying agents, antioxidant agents, filmogen agents and emulsifying agents;
to obtain spray-dried particles consisting in said OA, or particles comprising said OA and at least one additional element,
    spraying on said particles a water soluble or organic solvent, in particular ethanol, soluble EA, to obtain particles surrounded by said EA;
    drying said particles surrounded by said EA, to obtain microcapsules with a water insoluble coating, said water insoluble coating surrounding a core comprising said OA, and optionally at least one additional element,
said OA being superoxydismutase (SOD), in particular freeze-dried SOD or spray-dried SOD, said water soluble or organic solvent-soluble EA being in particular lac gum, said lac gum being in particular dissolved in water or ethanol.

In an advantageous embodiment, the present invention relates to a process wherein said spray-drying step, spraying step and drying step are done in a spray-dryer.

In an advantageous embodiment, the present invention relates to a process wherein said spray-drying step is done in a spray-dryer and said spraying step and drying step are done in a coating device by spray, in particular a coating device by spray comprising a fluidized bed.

Examples of spray-dryer wherein the spray-drying step can be performed are single effect spray-drying towers, toll form spray-drying towers, belt dryer and multiple effect spray-drying towers with internal or external fluid bed.

Examples of device wherein the spraying step can be performed are fluidized beds, top spray, tangential spray, bottom spray or wurster devices, batch process devices or continuous devices as horizontal fluid bed or multicellular fluid bed; these devices being as described in Vandamme et al Microencapsulation; Tec & Doc; 2007; Chapter 10.

In another aspect, the present invention relates to a food composition comprising microcapsules described above, provided said food composition is not a fermented dairy food composition.

In another aspect, the present invention relates to a beverage composition comprising microcapsules described above, provided said beverage composition is not a fermented dairy food composition.

In an advantageous embodiment, the present invention relates to a food composition comprising microcapsules described above, provided said food composition is not a fermented dairy food composition and said food composition does not comprise vitamin C or a chemical derivative of vitamin C.

In an advantageous embodiment, the present invention relates to a beverage composition comprising microcapsules described above, provided said beverage composition is not a fermented dairy food composition and said beverage composition does not comprise vitamin C or a chemical derivative of vitamin C.

In an advantageous embodiment, the present invention relates to a food composition comprising unfermented dairy products.

In an advantageous embodiment, the present invention relates to a beverage composition comprising unfermented dairy products, in particular milk.

In an advantageous embodiment, the present invention relates to a food composition comprising a vegetal milk, in particular almond, coconut, rice and soy milk, said composition being unfermented or fermented.

In an advantageous embodiment, the present invention relates to a beverage composition comprising a vegetal milk, in particular almond, coconut, rice and soy milk, said composition being unfermented or fermented.

In an advantageous embodiment, the present invention relates to a food composition comprising one or more fruits in addition of said microcapsules.

In an advantageous embodiment, the present invention relates to a beverage composition comprising one or more fruits in addition of said microcapsules.

In an advantageous embodiment, the present invention relates to a food composition wherein said food composition is a fruit juice composition.

In an advantageous embodiment, the present invention relates to a beverage composition wherein said beverage composition is a fruit juice composition.

In an advantageous embodiment, the present invention relates to a food composition comprising one or more vegetables in addition of said microcapsules.

In an advantageous embodiment, the present invention relates to a beverage composition comprising one or more vegetables in addition of said microcapsules.

In an advantageous embodiment, the present invention relates to a food composition comprising:
    said microcapsules,
    water,
    one or more sugar and/or sweetener
    flavoring(s).

In an advantageous embodiment, the present invention relates to a beverage composition comprising:
said microcapsules,
water,
one or more sugar and/or sweetener
flavoring(s).

In an advantageous embodiment, the present invention relates to a beverage composition comprising:
said microcapsules, wherein said OA is in particular SOD,
water,
optionally a fruit juice,
optionally at least one vitamin, in particular vitamin C riboflavin,
optionally proteins.

In an advantageous embodiment, the present invention relates to a pulverulent composition for the preparation of an instant drink comprising:
said microcapsules, wherein said OA is in particular SOD,
optionally at least one vitamin, in particular vitamin C or riboflavin,
optionally proteins,
said pulverulent composition to be mixed with water and/or at least a fruit juice before use.

In another aspect, the present invention relates to a cosmetic composition comprising microcapsules described above.

In another aspect, the present invention relates to a pharmaceutical composition comprising microcapsules described above.

In another aspect, the present invention relates to the use of microcapsules described above for the preparation of a food composition.

In another aspect, the present invention relates to the use of microcapsules described above for the preparation of a cosmetic composition.

In another aspect, the present invention relates to the use of microcapsules described above for the preparation of a pharmaceutical composition.

Said SEM analyses were performed with a Quanta200, ESEM FEG type microscope (Scanning Electron Microscopes, Field emission gun), at a water vapor pressure of 1.2 mbar, a voltage of 20 kV and a current density of 4 (on a scale ranging from 0 to 7).

Figure 1:
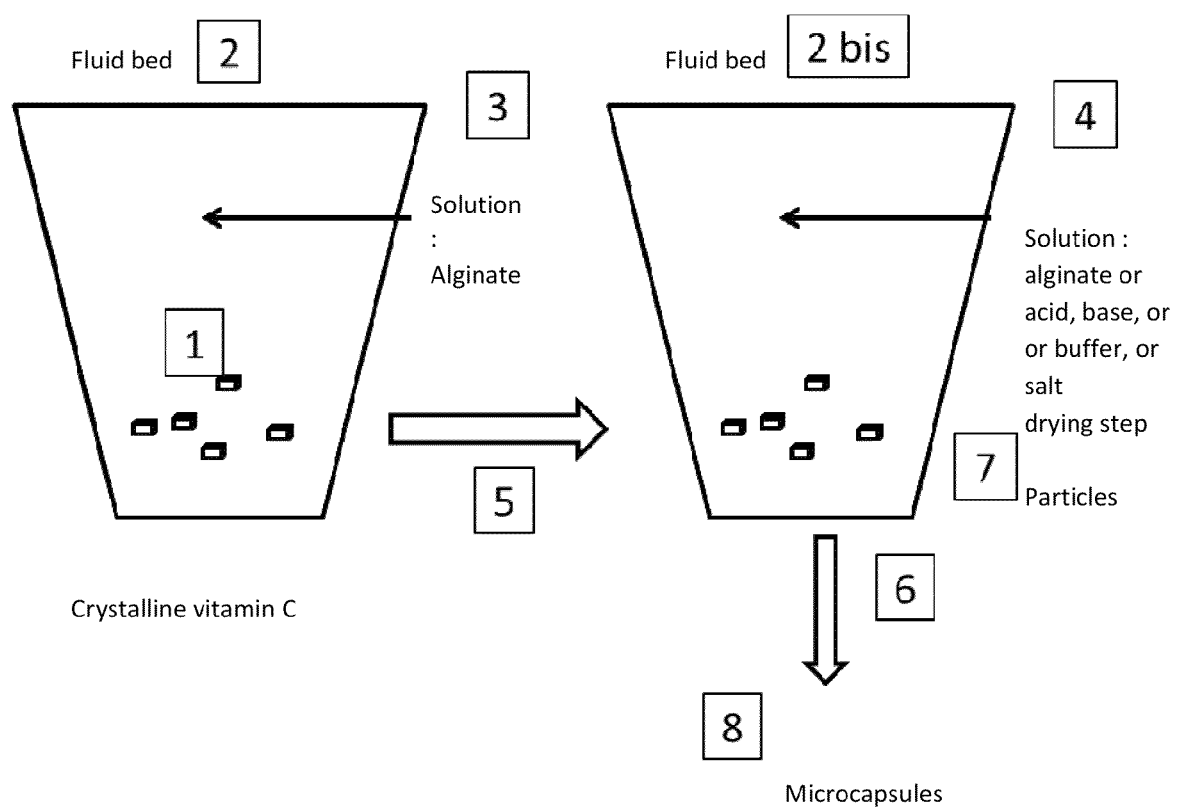
FIG. 1 presents a process wherein vitamin C particles in a crystalline form (1) are coated in a fluid bed (2) with an aqueous alginate solution (3) sprayed on said particles. Obtained particles (7) are then placed (5) in the same or another fluid bed (2bis). Alginate solution or acid or base or buffer or salt solution (4) is then sprayed on the particles (7) or the said particles are solely dried. Microcapsules (8) are recovered (6).
Figure 2:
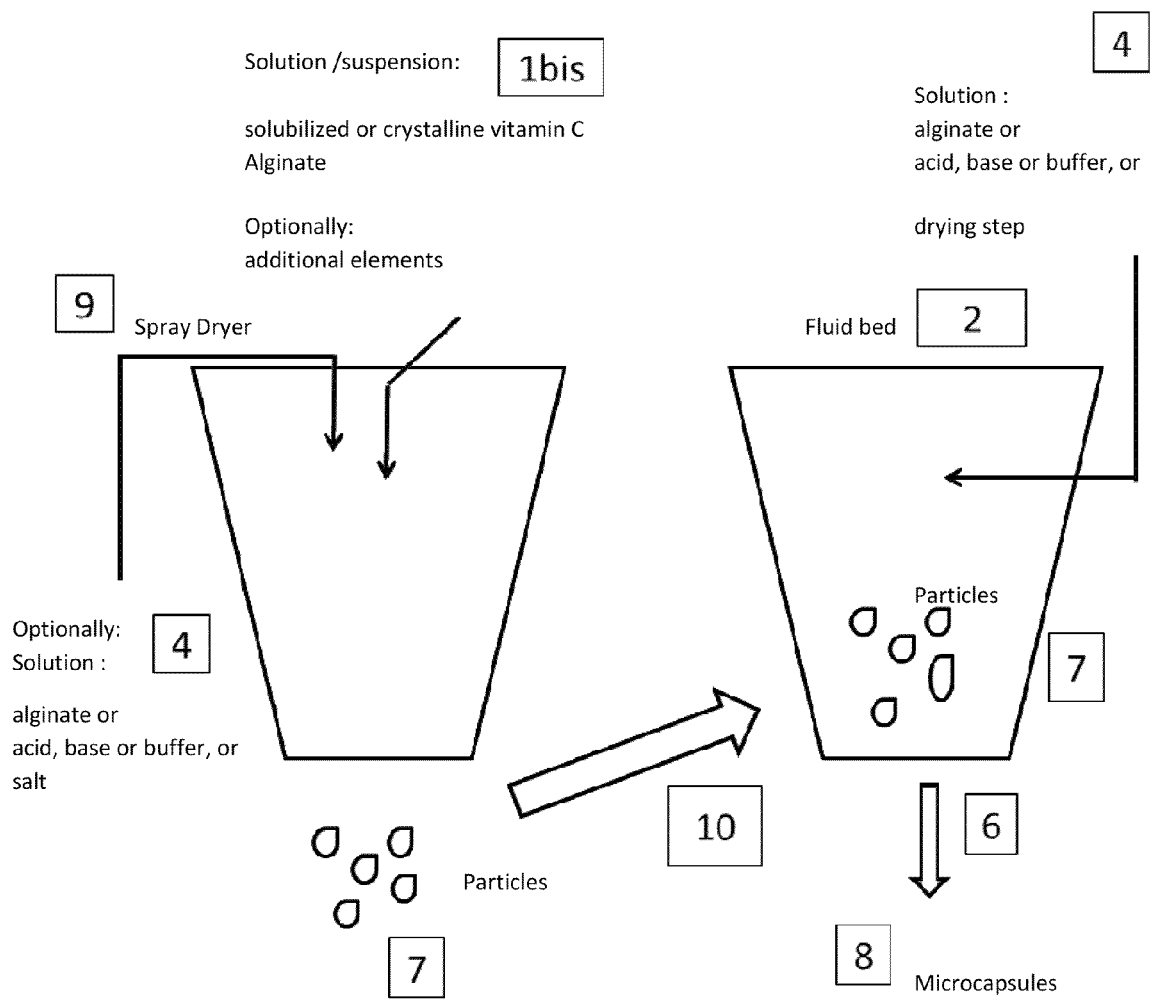
FIG. 2 presents a process wherein, alginate and optionally addition elements are solubilized in water, with solubilized or fruit juice vitamin C: solution (1bis), or with crystalline vitamin C: suspension (1Bis) and then sprayed in the spray-dryer (9). Either the obtained particles (7) are then transferred (10) in a fluid bed (2bis) and an alginate solution or acid or base or buffer or salt solution (4) is sprayed on said particles (7), or an alginate solution or acid or base or buffer solution (4) is in parallel sprayed in the same said spray dryer (9), and then optionally dried. Microcapsules (8) are recovered (6).
Figure 3:
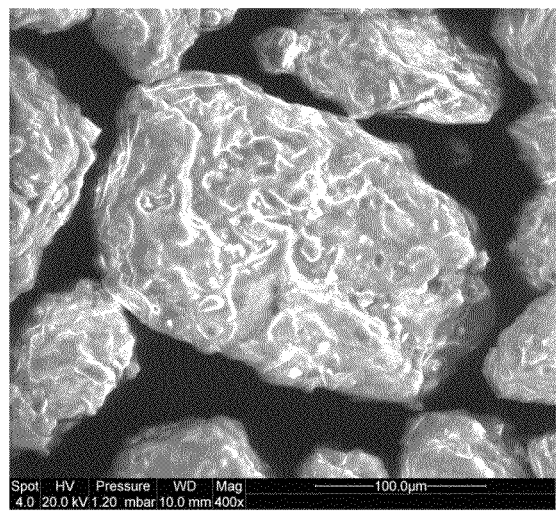
FIGS. 3, 4 and 5 present scanning electron microscope (SEM) analyses of microcapsules obtained by the process respectively described in example 4, 2 and 3.
Figure 4:
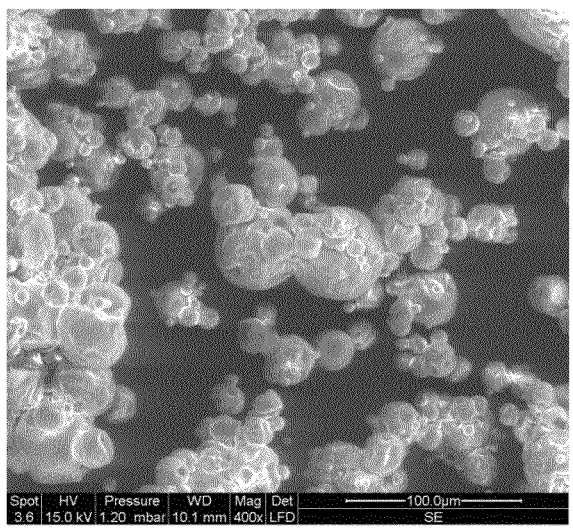
Figure 5:
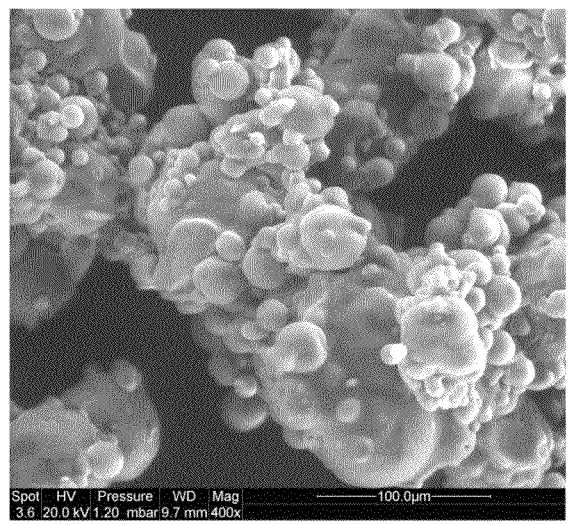
Figure 6:
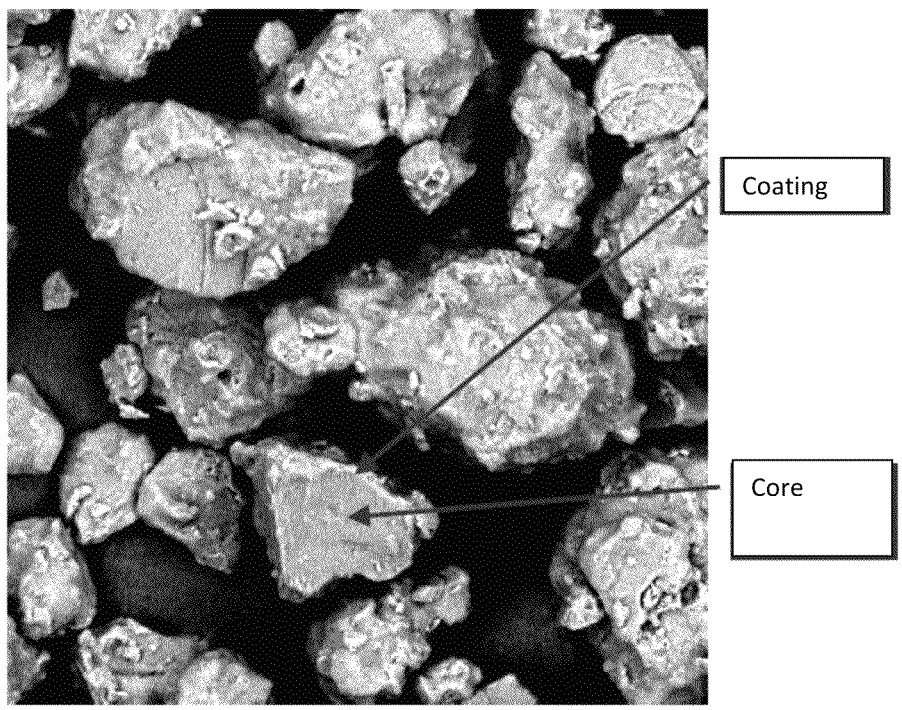
FIG. 6 present scanning electron microscope (SEM) analysis of a microcapsule obtained by the process described in example 1, which was fractured prior to said analysis.
Figure 7A:
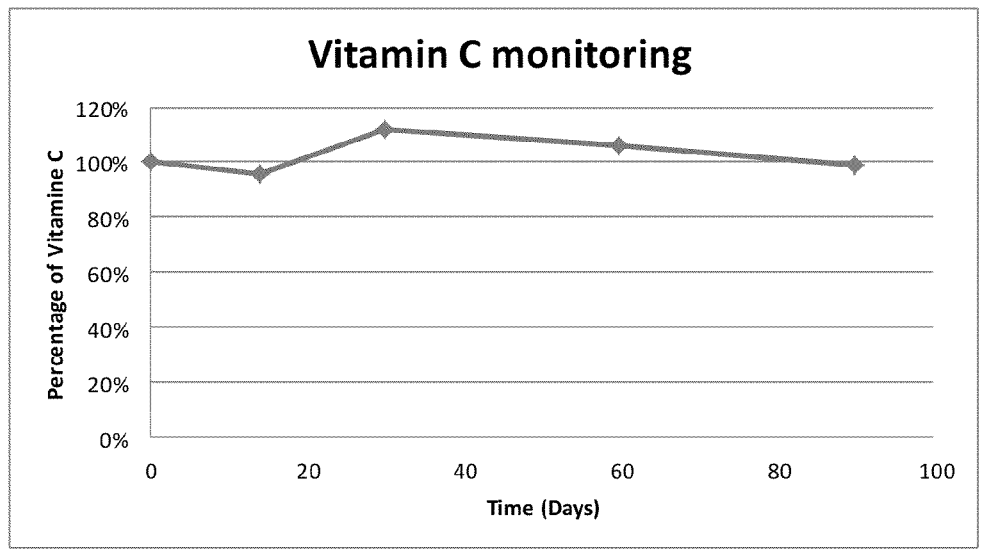

FIG. 7A presents the vitamin C monitoring on a microcapsule obtained by the process described in example 4.

Said microcapsules were packed in heat-sealed aluminum bags, stored at 4° C. or 20° C. and monitored over time, over a period of 3 months. The results show that there is no degradation of vitamin C content after 3 months of storage. Vitamin C monitoring was performed according to standard NF 14130 (by HPLC).

Figure 7B:
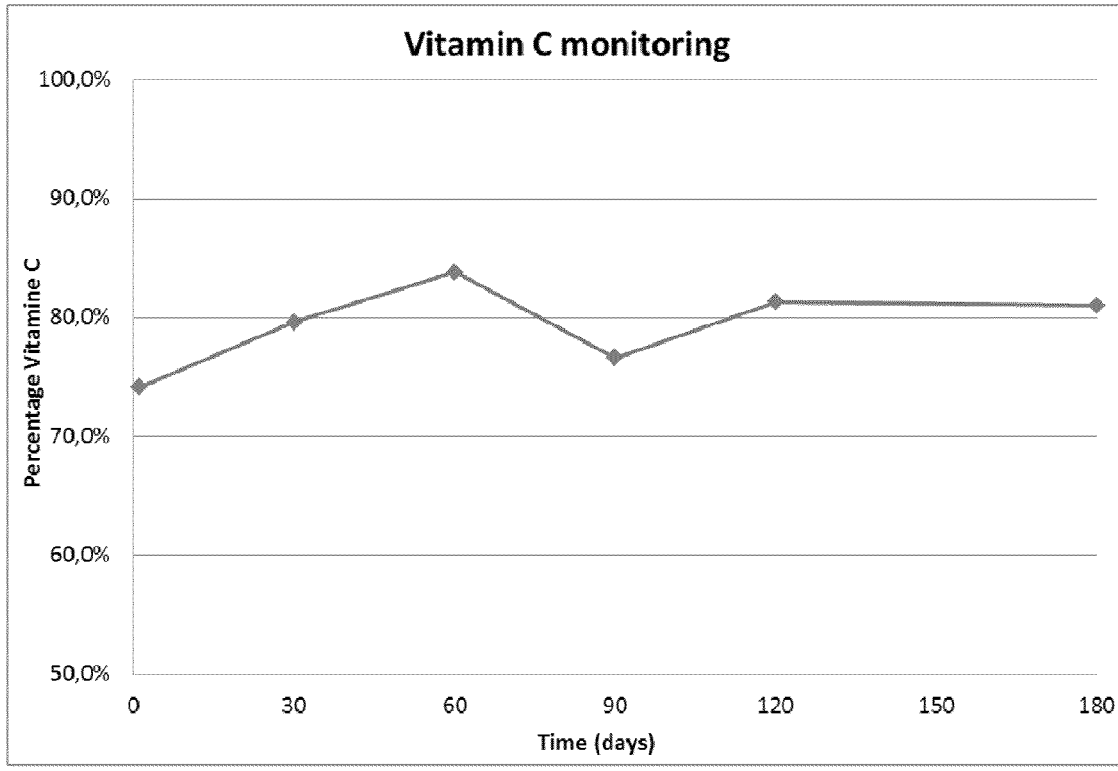

FIG. 7B presents the vitamin C monitoring on a microcapsule obtained by the process described in example 4.

Said microcapsules were packed in heat-sealed aluminum bags, stored at 4° C. or 20° C. and monitored over time, over a period of 6 months. The results show that there is no degradation of vitamin C content after 6 months of storage. Vitamin C monitoring was performed according to standard NF 14130 (by HPLC).

Figure 8:
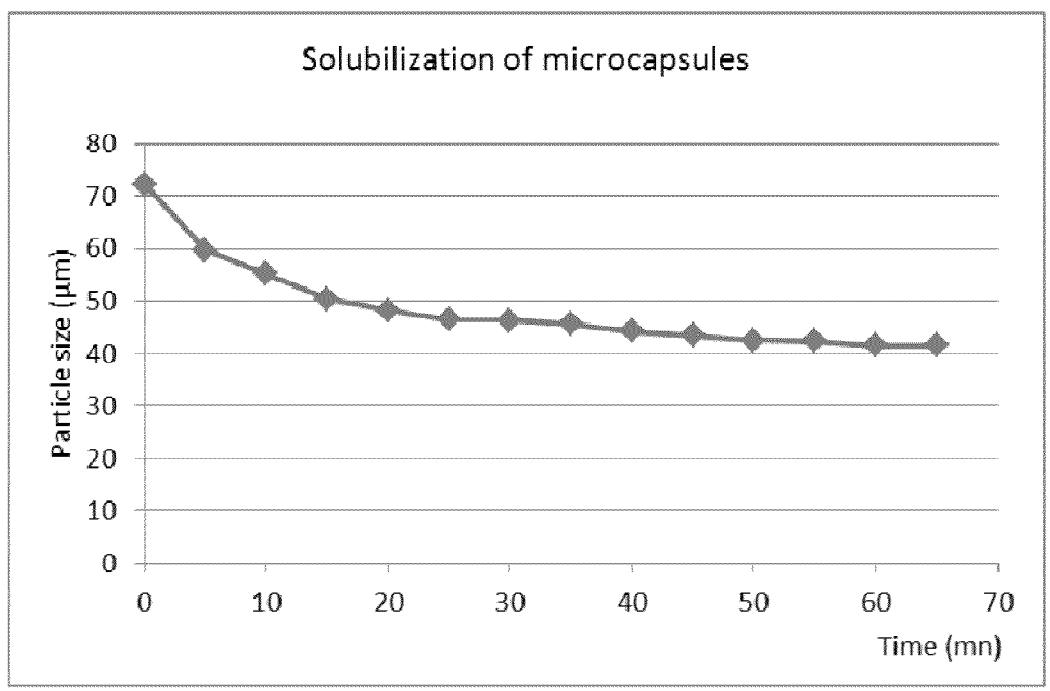

FIG. 8 presents the following of the size of microcapsule obtained by the process described in example 4 over time, when said microcapsules are placed in water at room temperature. Size is expressed in D(v; 0.5) in microns and is measured using a laser particle sizer Malvern Instrument, MSS Type, model MasterSizer, D(v; 0.5) being the mean particle size of the obtained microcapsule size distribution.

DETAILED DESCRIPTION OF THE INVENTION

The present invention is further illustrated by the following examples.

EXAMPLES

Example 1

Microcapsules Containing Vitamin C 3.3 kg of crystalline vitamin C were fluidized in a fluid bed (WSG5 GLATT), inlet air temperature is 60° C.

2.9 kg of a 5% solution of sodium alginate in dry matter, containing 10 g of ascorbyl palmitate were sprayed on the fluidized particles with a bifluid nozzle (spraying system SS 2050), on a top-spray position, as well known by those skilled in the art (in particular Vandamme et al *Microencapsulation*; Tec & Doc; 2007), and then dried. Solid particles are obtained.

Another 1.1 Kg of a 5% solution of sodium alginate in dry matter was then spray dried on the fluidized particles. A final drying step of 30 mn was then processed at a maximum temperature of 50° C. on the microcapsules.

The final microcapsules had a moisture content of 1.1% (infrared measurement). Particle size distribution was below 300 μm (mean particle size measured by light diffraction on Malvern sizer) and bulk density was of 850 g/l.

Example 2

Microcapsules Containing Vitamin C

A solution was prepared with 7.8 kg of crystalline vitamin C in 31.2 kg of water at room temperature. 3.78 kg of modified starch, 0.5 kg of carboxymethylcellulose and 0.8 kg of alginate were added to this preparation. The preparation was then homogenized at a pressure of 200 bars. The homogenized preparation was then dried in a single stage dryer (Minor production tower, GEA-NIRO) with a rotary atomizer, with an inlet temperature of 150° C. and outlet temperature of 85° C. Solid particles are obtained.

4.6 kg of a calcium chloride solution at 5% dry matter was then sprayed on the fluidized particles on a fluidized bed (WSG5, GLATT) as well known by those skilled in the art.

The final microcapsules had an average size of 210 μm (mean particle size measured by light diffraction on Malvern sizer), a moisture content of 2.3% and a bulk density of 650 g/l.

Example 3

Microcapsules Containing Vitamin C from Acerola Juice 2.6 kg of acerola fruit juice, with a vitamin C content of 20.9 g/100 ml, was mixed with 0.6 kg of starch, 0.08 kg of carboxy methyl cellulose, 0.10 kg of alginate and 7.8 kg of water.

The preparation was homogenized at 200 bars.

The homogenized preparation was then dried in a single stage dryer (Minor production tower, GEA-NIRO) with a rotary atomizer, with an inlet temperature of 125° C. and outlet temperature of 90° C. Solid particles are obtained.

0.6 kg of a calcium chloride solution at 5% dry matter was then sprayed on the fluidized particles on a fluidized bed (WSG5, GLATT) as well known by those skilled in the art.

The final microcapsules had an average size of 80 μm (mean particle size measured by light diffraction on Malvern sizer), a moisture content of 5% and a hulk density of 630 g/l.

Example 4

Microcapsules Containing Vitamin C 3.3 kg of crystalline vitamin C, were fluidized in a fluid bed (WSG5 GLATT), inlet air temperature is 60° C.

2.9 kg of a 5% solution of sodium alginate in dry matter, containing 10 g of ascorbyl palmitate were sprayed on the fluidized particles with a bifluid nozzle (spraying system SS 2050), on a top-spray position, as well known by those skilled in the art (in particular Vandamme et al *Microencapsulation*; Tec & Doc; 2007). Solid particles are obtained.

0.8 Kg of a calcium chloride solution, 5% dry matter was then spray dried on the fluidized particles. The final microcapsules had a moisture content of 2.8% (infrared measurement). Particle size distribution was below 300 μm (mean particle size measured by light diffraction on Malvern sizer) and bulk density was of 800 g/l.

Example 5

Microcapsules Containing Vitamin C

A solution was prepared with 7.8 kg of crystalline vitamin C in 31.2 kg of water at room temperature. 3.78 kg of modified starch, 0.5 kg of carboxymethylcellulose and 0.8 kg of alginate were added to this preparation. The preparation was then homogenized at a pressure of 200 bars. 4.6 kg of a calcium chloride solution at 5% dry matter was prepared. The homogenized preparation was then sprayed in a single stage dryer (Minor production tower, GEA-NIRO) with a rotary atomizer, and the calcium chloride solution was also sprayed in the same time in the chamber of the same dryer. Drying step was made with an inlet temperature of 150° C. and outlet temperature of 75° C.

The final microcapsules had an average size of 80 μm (mean particle size measured by light diffraction on Malvern sizer), a moisture content of 6.0% and a bulk density of 600 g/l.

Example 6

Microcapsules Containing Omega 3 Enriched Oil 1.3 kg of omega 3 enriched oil was mixed with 3.8 kg of modified starch, 0.7 kg of Carboxymethylcellulose, 0.8 kg of alginate and 11.8 kg of water.

The preparation was homogenized at 200 bars.

The homogenized preparation was then dried in a single stage dryer (Minor production tower, GEA-NIRO) with a rotary atomizer, with an inlet temperature of 150° C. and outlet temperature of 80° C. Particles with a solid outer part are obtained.

4.1 kg of a calcium chloride solution at 5% dry matter was then sprayed on the fluidized particles on a fluidized bed (WSG5, GLATT) as well known by those skilled in the art.

The final microcapsules had an average size of 80 μm (mean particle size measured by light diffraction on Malvern sizer), a moisture content of 3.2% and a bulk density of 470 g/l.

Example 7

Microcapsules Containing Vitamin C Coated with Ethylcellulose 2.47 kg of crystalline vitamin C were fluidized in a fluid bed (WSG5, GLATT). Inlet temperature did not exceed 40° C.

2.47 kg of ethylcellulose were prepared in ethanol at 10% dry matter and sprayed using a bifluid nozzle (spraying system SS 2050), on a top spray position on the fluidized crystalline vitamin.

After the coating, the microcapsules were dried in the fluidized bed chamber for 10 mn.

The final microcapsules had a moisture content of 1.1% (infrared moisture measurement, 105° C.) and a particle size distribution of 130 μm (mean particle size measured by light diffraction on Malvern sizer).

Example 8

Microcapsules Containing SOD 3.3 kg of freeze dried superoxydismutase enzyme (SOD) were fluidized in a fluid bed (WSG5, GLATT). Inlet temperature was 60° C.

2.9 kg of a 5% solution of sodium alginate in dry matter, containing 10 g of ascorbyl palmitate were sprayed on the fluidized particles with a bifluid nozzle (spraying system SS 2050), on a top-spray position, as well known by those skilled in the art (in particular Vandamme et al *Microencapsulation*; Tec & Doc; 2007). Solid particles are obtained.

0.8 Kg of a calcium chloride solution, 5% dry matter was then spray dried on the fluidized particles.

The final microcapsules had a moisture content of 1.3%. Particle size distribution was below 300 μm (mean particle size measured by light diffraction on Malvern sizer) and bulk density was of 410 g/l.

Example 9

Microcapsules Containing SOD Coated with Lac Gum 500 g of freeze-dried of superoxydismutase enzyme (SOD) were weighted and put into a fluid bed (GPCG1, GLATT) and fluidized. 516 g of Lac gum (ie: 500 g of Dry Lac gum) were dissolved at 20% dry matter and sprayed on the fluidized SOD. Process temperature of the powder did not exceed 36° C. Final product had a moisture content of 2.1% and an average particle size mean of 370 μm (Median diameter Dv (0.5) measured by laser particle sizer Malvern)

Analyses of SOD activity were made in water solution at pH 2.9 and 7.0.

No SOD activity was observed at pH 2.9 although more than 95% of SOD activity is recovered at pH 7.0.

Example 10

Microcapsules Containing Ferrous Ascorbate 1.2 kg of ferrous ascorbate were weighted and put into a fluid bed (GPCG1, GLATT), inlet air temperature is 80° C.

1.1 kg of a 5% solution of sodium alginate in dry matter were sprayed on the fluidized particles with a bifluid nozzle, on a top-spray position. Solid particles are obtained.

0.3 Kg of a calcium chloride solution, 5% dry matter was then spray dried on the fluidized particles.

The final microcapsules had a moisture content of 6%. Particle size distribution was below 300 μm (mean particle size measured by light diffraction on Malvern sizer) and bulk density was of 420 g/l.

Example 11

Microcapsules Containing DHA 500 g of crystalline Dihydroxyacetone (DHA) were weighted and put into a fluid bed (GPCG1, GLATT) and fluidized. 125 g of Lac gum were dissolved at 24% dry matter and sprayed on the fluidized DHA.

The microcapsules obtained had a moisture content of 4.1%, and a particle size distribution of 790 μm (mean diameter, measured by laser diffraction on Malvern sizer)

Evaluation of coloration was made in water at pH 4.0 and 7.0.

No coloration occurred after 1H at pH 4.0, although in water at pH 7.0 an orange coloration appeared in the first 15 mn and became brownish after 1H showing the protective effect of the microcapsule of the invention in low pH conditions.

Example 12

Microcapsules Containing SOD Coated with Lac Gum (50% Encapsulation)

500 g of freeze-dried superoxydismutase enzyme (SOD) were weighted and put into a fluid bed (GPCG1, GLATT) and fluidized. 516 g of Lac gum (ie: 500 g of Dry Lac gum) were dissolved at 27% dry matter in water and sprayed on the fluidized SOD. Process temperature of the powder did not exceed 39° C. Final product had a moisture content of 3.4% and an average particle size mean of 470 μm (Median diameter Dv (0.5) measured by laser particle sizer Malvern).

Analyses of SOD activity were made in water solution at pH 2.9 and 7.0.

Less than 5% SOD activity was observed at pH 2.9 although more than 94% of SOD activity is recovered at pH 7.0.

Example 13

Microcapsules Containing SOD Coated with Lac Gum (50% Encapsulation)

500 g of freeze-dried of superoxydismutase enzyme (SOD) were weighted and put into a fluid bed (GPCG1, GLATT) and fluidized. 516 g of Lac gum (ie: 500 g of Dry Lac gum) were dissolved at 10% dry matter in ethanol and sprayed on the fluidized SOD. Process temperature of the powder did not exceed 36° C. Final product had a moisture content of 1.9% and an average particle size mean of 330 μm (Median diameter Dv (0.5) measured by laser particle sizer Malvern).

Analyses of SOD activity were made in water solution at pH 2.9 and 7.0.

No SOD activity was observed at pH 2.9 although more than 94% of SOD activity is recovered at pH 7.0.

Example 14

Microcapsules Containing SOD Coated with Lac Gum (30% Encapsulation)

490 g of freeze-dried superoxydismutase enzyme (SOD) of enzyme activity of 81.6 U/mg were weighted and put in a fluid bed (GPCG1, GLATT) and fluidized. 216 g of Lac gum (ie: 210 g of dry Lac gum) were dissolve at 20% dry matter in ethanol and sprayed on the fluidized SOD. Process temperature do not exceed 40° C.

Final product has a moisture content of 2.8% and an average particle size of 250 μm (Median diameter Dv (0.5) measured by laser particle sizer Malvern).

Analysis of SOD made in a solution of 230 mg of the final product in 30 g of water at pH 4.0 and room temperature, gives a measurement of SOD activity in the solution of less than 1 U/mg in the solution after 15 mn (less than 2% of the SOD encapsulated in the microcapsule). The same measurement made in a solution containing 230 mg of the final product in 30 g of tap water at ph 7.0 and room temperature, gives a measurement of SOD activity in the solution of 44 U/mg in the solution after 15 mn (ie: 77% of the SOD encapsulated in the microcapsule).

Example 15

Microcapsules Containing SOD Coated with Lac Gum (50% Encapsulation)

500 g of freeze-dried superoxydismutase enzyme (SOD) were weighted and put in a fluid bed (GPCG1, GLATT) and fluidized. 516 g of Lac, gum (ie: 500 g of dry Lac gum were dissolve at 20% dry matter in ethanol and sprayed on the fluidized SOD. Process temperature does not exceed 36° C.

Final product has a moisture content of 2.5% and an average particle size of 210 μm (Median diameter Dv (0.5) measured by laser particle sizer Malvern).

Analysis of SOD made in a solution of 230 mg of the final product in 30 g of water at pH 4.0 and room temperature, gives a measurement of SOD activity in the solution of less than 2 U/mg in the solution after 15 mn (less than 4% of the SOD encapsulated in the microcapsule). The same measurement made in a solution containing 230 mg of the final product in 30 g of tap water at ph 7.0 and room temperature, gives a measurement of SOD activity in the solution of 23 U/mg in the solution after 15 mn (ie: 58% of the SOD encapsulated in the microcapsule).

Example 16

Microcapsules Containing SOD Coated with Lac Gum (30% Encapsulation)

400 g of spray-dried superoxydismutase enzyme (SOD) were weighted and put into a fluid bed (GPCG1, GLATT) and fluidized. 176 g of Lac gum (ie: 171 g of Dry Lac gum) were dissolved at 10% dry matter in ethanol and sprayed on the fluidized SOD. Process temperature of the powder did not exceed 34° C. Final product had a moisture content of 2.8% and an average particle size mean of 320 µm (Median diameter Dv (0.5) measured by laser particle sizer Malvern).

Analyses of SOD activity were made in water solution at pH 2.9 and 7.0.

Less than 3% SOD activity was observed at pH 2.9 although more than 89% of SOD activity was recovered at pH 7.0.

Example 17

Composition for Food Supplement Use 317 g of microcapsules of example 16 were mixed to 685 g of maltodextrins to obtain a composition of 14 UI/mg. 60 mg of this composition was then packed into gelatin capsules for food supplement use.

Example 18

Microcapsules Containing SOD Coated with Lac Gum (50% Encapsulation)

500 g of spray-dried superoxydismutase enzyme (SOD) were weighted and put into a fluid bed (GPCG1, GLATT) and fluidized. 516 g of Lac gum (ie: 500 g of Dry Lac gum) were dissolved at 27% dry matter in water and sprayed on the fluidized SOD. Process temperature of the powder did not exceed 39° C. Final product had a moisture content of 3.2% and an average particle size mean of 450 µm (Median diameter Dv (0.5) measured by laser particle sizer Malvern).

Analyses of SOD activity were made in water solution at pH 2.9 and 7.0.

Less than 5% SOD activity was observed at pH 2.9 although more than 96% of SOD activity is recovered at pH 7.0.

Example 19

Microcapsules Containing Calcium Ascorbate 1.2 kg of crystalline Calcium Ascorbate were fluidized in a fluid bed (GPCG1 GLATT), inlet air temperature is 70° C.

Then, 1.65 kg of a 5% solution of sodium alginate in dry matter, containing 3 g of ascorbyl palmitate were sprayed on the fluidized particles with a bifluid nozzle (spraying system SS 2050), on a top-spray position, as well known by those skilled in the art (in particular Vandamme et al *Microencapsulation*; Tec & Doc; 2007), and then dried. Solid, particles are obtained.

Another 480 g of a 5% solution of calcium chloride in dry matter was then spray dried on the fluidized particles. Solid particles are obtained A final drying step of 30 mn was then processed at a maximum temperature of 50° C. on the microcapsules.

The final microcapsules had a moisture content of 1.2% (infrared measurement). Particle size distribution was below 500 µm (mean particle size measured by light diffraction on Malvern sizer) and bulk density was of 830 g/l.

Example 20

Microcapsules Containing SOD Coated with Lac Gum 500 g of freeze-dried superoxydismutase enzyme (SOD) were weighted and put into a fluid bed (GPCG1, GLATT) and fluidized. 516 g of Lac gum (ie: 500 g of Dry Lac gum) were solubilized and sprayed on the fluidized SOD. Process temperature of the powder did not exceed 35° C. Final product had a moisture content of 2.1% and an average particle size mean of 210 µm (Median diameter Dv (0.5) measured by laser particle sizer Malvern).

Analyses of SOD activity were made in water solution at pH 2.9 and 7.0.

Less than 1% SOD activity was observed at pH 2.9 although more than 95% of SOD activity was recovered at pH 7.0 after 1H Example 2

Preparation of a Beverage Composition Comprising Microcapsules Containing SOD Coated with Lac Gum and Orange Juice 40 mg of microcapsules obtained in example 20 were added to a serving bottle of 100 ml of orange fruit juice, at pH=3.7. The mix was shaken 10 sec (usual time needed before drinking such a beverage) and then SOD activity was measured. No SOD activity was founded in the juice, meaning that no SOD was released in the fruit juice during the preparation of the beverage with SOD.

Example 22

Pulverulent Composition for the Preparation of an Instant Drink 10 mg of microcapsules of example 20 were mixed with the following powders: 0.2 g of xanthan gum, 0.8 g of glucose syrup DE38, and 1 g of sucrose. The whole mix was packed in a stick. The stick was added to 100 ml of mineral water pH=6.9, and stirred gently during 10 sec. Analysis of the SOD activity in the solution after 15 mn was less than 3% of the total activity of the 10 mg of SOD showing that almost no release of SOD appeared during the preparation of such an instant drink. The time release of the SOD is long enough to allow ingestion of almost the whole SOD activity given.

Example 23

Preparation of a Beverage Composition Comprising Microcapsules Containing SOD Coated with Lac Gum and Apple Juice 1.2 g of microcapsules of example 20 were added to 10 L of freshly pressed apple juice pH=3.9 and dispersed and stirred in the juice during 1 mn. These 10 L of preparation were pasteurized at 70° C. during 15 sec and then packed in closed bottles, and cooled to less than 30° C. in 10 mn. Analysis of the SOD activity in the apple juice was made after 1 day and 1 month. No SOD activity was founded in the juice. Analysis were made neutralizing the juice to pH 7.5; more than 50% of the total activity of the SOD was recovered when extracting the SOD from the microcapsules in the apple juice at neutral showing that no release of SOD occurred in this acid fruit juice drinks.

Example 24

Preparation of a Beverage Composition Comprising Microcapsules Containing SOD Coated with Lac Gum and a Liquid Unfermented Product 40 mg of microcapsules of example 20 were added to 100 ml of a liquid unfermented dairy product pH 4.4 and shake during 5 sec. Analysis of the SOD activity in the dairy beverage was less than 2% of the total activity of the 40 mg of SOD showing that almost no release of SOD appeared during the preparation of such an instant drink.

Example 25

Microcapsules Containing Oxidizable Oil 349 g of tocopherol acetate was mixed with 160 g of modified starch, 247 g of maltodextrin, 40 g of alginate and 1.22 kg of water.

The preparation was homogenized at 200 bars.

Another 8 g of a calcium chloride aqueous solution at 5% dry matter was prepared.

The homogenized preparation was then sprayed in a single stage dryer (Minor production tower, GEA-NIRO) combined with the calcium chloride solution as a mean for insolubility with a trifluid nozzle. Drying was made with an inlet temperature of 120° C. and outlet temperature of 70° C.

The final microcapsules are insoluble and have a mean particle size of 80 μm (mean particle size measured by light diffraction on Malvern sizer), a moisture content of 3.2% and a bulk density of 470 g/l.

The invention claimed is:

1. Microcapsule comprising:
a core comprising superoxide dismutase (SOD), and
a coating surrounding the core, wherein the coating comprises lac gum, wherein the coating is water insoluble in acidic conditions and is water soluble in basic or neutral conditions.

2. Microcapsule according to claim 1, wherein said coating is such that, when said microcapsule is placed in an alimentary, cosmetically or pharmaceutically acceptable medium:
the SOD is not degraded by element(s) of said medium, and
said element(s) of the medium is (are) not degraded by the SOD.

3. Microcapsule according to claim 1, wherein the mass of said coating is from 3 to 50% of the total mass of said microcapsule.

4. Microcapsule according to claim 1, wherein said microcapsule has a size in a range of from 1 μm to 3 mm.

5. Microcapsule according to claim 1, wherein the SOD is in a crystalline state.

6. The microcapsule according to claim 1, with the proviso that:
the core does not comprise a metal oxide, and
the coating does not comprise a disintegrant.

7. The microcapsule according to claim 1, wherein an outer portion of the core is in a solid form.

8. The microcapsule according to claim 1, wherein the mass of the coating is from 5 to 8% of the total mass of the microcapsule.

9. The microcapsule according to claim 1, wherein the mass of the coating is from 4 to 12% of the total mass of the microcapsule.

10. The microcapsule according to claim 1, wherein the microcapsule has a size in a range of from 50 μm to 200 μm.

11. The microcapsule according to claim 1, wherein the microcapsule has a size in a range of from 20 μm to 500 μm.

12. The microcapsule according to claim 1, wherein the SOD is in an amorphous state.

13. The microcapsule according to claim 1, wherein an inner portion of the core comprises the SOD, the SOD being in a liquid form.

14. The microcapsule according to claim 13, wherein the SOD is in an oily form, a viscous oil form or a pasty form.

15. The microcapsule according to claim 1, wherein the core is crystalline.

16. The microcapsule according to claim 1, wherein the core is amorphous.

17. The microcapsule according to claim 1, having a water content of less than 6% by weight of the microcapsule.

18. Food or beverage composition comprising the microcapsules according to claim 1, provided said food or beverage composition is not a fermented dairy food composition.

19. Pulverulent composition for the preparation of an instant drink comprising:
the microcapsules according to claim 1,
optionally at least one vitamin, and
optionally proteins,
said pulverulent composition to be mixed with water and/or a fruit juice before use.

20. Microcapsule, consisting of:
a core consisting of superoxide dismutase (SOD), an outer portion of said core being in a solid form, and
a coating surrounding the core, the coating comprising a lac gum, wherein the coating is water insoluble in acidic conditions and is water soluble in basic or neutral conditions.

* * * * *